(12) United States Patent
Yagi et al.

(10) Patent No.: US 9,956,346 B2
(45) Date of Patent: May 1, 2018

(54) SYRINGE

(71) Applicant: DAICEL CORPORATION, Osaka (JP)

(72) Inventors: Toshiki Yagi, Himeji (JP); Masayuki Ueda, Tokyo (JP)

(73) Assignee: DAICEL CORPORATION, Osaka (JP)

( * ) Notice: Subject to any disclaimer, the term of this patent is extended or adjusted under 35 U.S.C. 154(b) by 0 days. days.

(21) Appl. No.: 15/389,272

(22) Filed: Dec. 22, 2016

(65) Prior Publication Data

US 2017/0100545 A1 Apr. 13, 2017

Related U.S. Application Data

(62) Division of application No. 14/400,534, filed as application No. PCT/JP2013/063171 on May 10, 2013, now Pat. No. 9,555,193.

(30) Foreign Application Priority Data

May 11, 2012 (JP) ................. 2012-109863

(51) Int. Cl.
    *A61M 5/30*     (2006.01)
    *A61M 5/24*     (2006.01)
    *A61M 5/315*     (2006.01)

(52) U.S. Cl.
    CPC ............... *A61M 5/30* (2013.01); *A61M 5/24* (2013.01); *A61M 5/3015* (2013.01); *A61M 5/31576* (2013.01); *A61M 2005/2411* (2013.01)

(58) Field of Classification Search
    CPC ............................. A61M 5/30; A61M 5/2046
    See application file for complete search history.

(56) References Cited

U.S. PATENT DOCUMENTS 6,013,050 A     1/2000    Bellhouse et al.
6,258,063 B1    7/2001    Haar et al.
(Continued)

FOREIGN PATENT DOCUMENTS

CN        1761496 A     4/2006
CN     103442755 A    12/2013
(Continued)

OTHER PUBLICATIONS

Office Action issued in corresponding Japanese Patent Application No. 2016-139588 dated Apr. 18, 2017.
(Continued)

*Primary Examiner* — Aarti B Berdichevsky
(74) *Attorney, Agent, or Firm* — Knobbe Martens Olson & Bear LLP

(57) ABSTRACT

A syringe includes a holding portion that accommodates an injection objective substance, a driving portion that applies injection energy, and a nozzle portion that includes a passage for injection, with these portions being loaded into a housing independently, whereby a state where the injection objective substance can be injected is established. The syringe includes a regulating means for regulating a loading position of the holding portion and the driving portion within the housing so that a loading state, where the holding portion and the driving portion are always loaded in the same order into the housing, is established for injection of the injection objective substance. Due to this, it is possible to facilitate injection of injection liquid ideal for various purposes and to improve user's convenience.

6 Claims, 6 Drawing Sheets

(56) References Cited

U.S. PATENT DOCUMENTS

| | | |
|---|---|---|
| 8,070,714 B2 | 12/2011 | Alexandre et al. |
| 9,555,193 B2 * | 1/2017 | Yagi ........................ A61M 5/24 |
| 2002/0058907 A1 | 5/2002 | Deboer et al. |
| 2003/0114789 A1 | 6/2003 | Haar et al. |
| 2003/0135155 A1 | 7/2003 | Alexandre et al. |
| 2003/0149396 A1 | 8/2003 | Alexandre et al. |
| 2004/0049151 A1 | 3/2004 | Lell |
| 2007/0167906 A1 | 7/2007 | Alexandre et al. |
| 2008/0154189 A1 | 6/2008 | Alexandre et al. |
| 2013/0237951 A1 | 9/2013 | Oda |
| 2014/0200512 A1 | 7/2014 | Oda |
| 2014/0296777 A1 | 10/2014 | Haitsuka et al. |
| 2015/0057607 A9 | 2/2015 | Oda |
| 2015/0100015 A1 | 4/2015 | Yagi et al. |
| 2016/0129190 A1 | 5/2016 | Haitsuka |

FOREIGN PATENT DOCUMENTS

| | | |
|---|---|---|
| DE | 102 15 297 A1 | 10/2003 |
| EP | 2671605 A1 | 12/2013 |
| JP | 10-507390 A | 7/1998 |
| JP | 2003-535654 A | 12/2003 |
| JP | 2004-500933 A | 1/2004 |
| JP | 2005-523679 A | 8/2005 |
| JP | 2006-523484 A | 10/2006 |
| JP | 2007-525192 A | 9/2007 |
| JP | 2008-508881 A | 3/2008 |
| JP | 2008-206477 A | 9/2008 |
| JP | 2010-503616 A | 2/2010 |
| JP | 2012-065920 A | 4/2012 |
| JP | 2013-236675 A | 11/2013 |
| WO | WO 00/06228 | 2/2000 |
| WO | WO 01/78810 A1 | 10/2001 |
| WO | WO 2003/004620 A2 | 1/2003 |
| WO | WO 2005/019453 A2 | 3/2005 |
| WO | WO 2006/015373 A2 | 2/2006 |
| WO | WO 2008/047243 A2 | 4/2008 |
| WO | WO 2012/039454 A1 | 3/2012 |

OTHER PUBLICATIONS

International Search Report dated Jun. 25, 2013, received in International Application No. PCT/JP2013/063171.

Extended European Seearch Report (EESR), dated Jan. 22, 2016, received in corresponding European Patent Application No. 13788583.6.

Chinese Office Action, dated Feb. 29, 2016, received in corresponding Chinese Patent Application No. 201380036896.2.

Extended European Search Report dated Feb. 5, 2018 in related European Application No. 17195065.2.

* cited by examiner

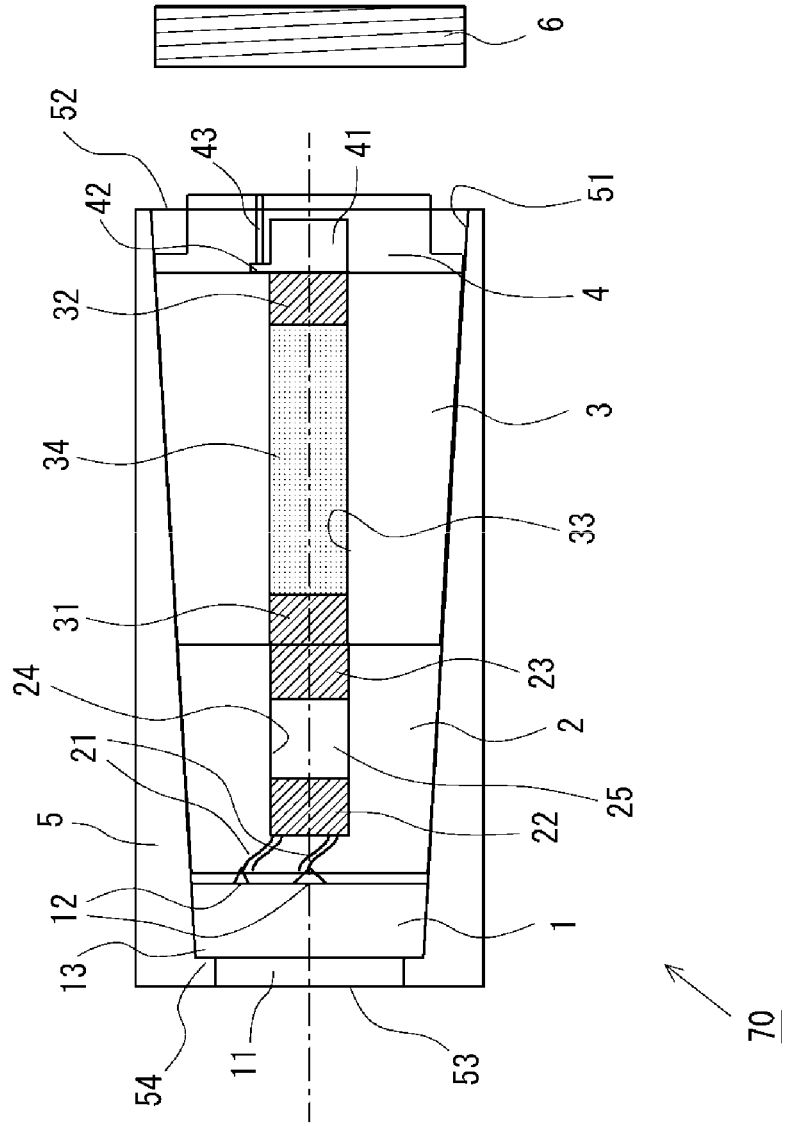
[Fig. 1]

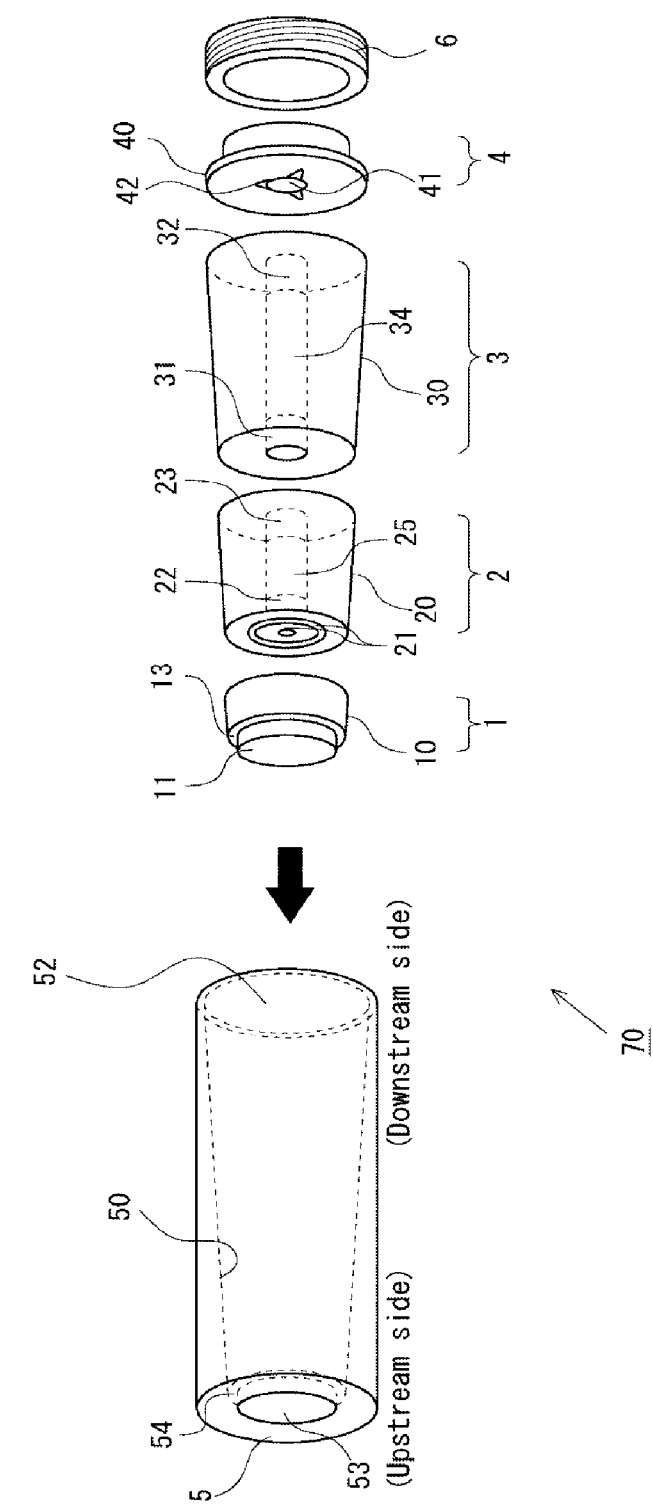
[Fig. 2]

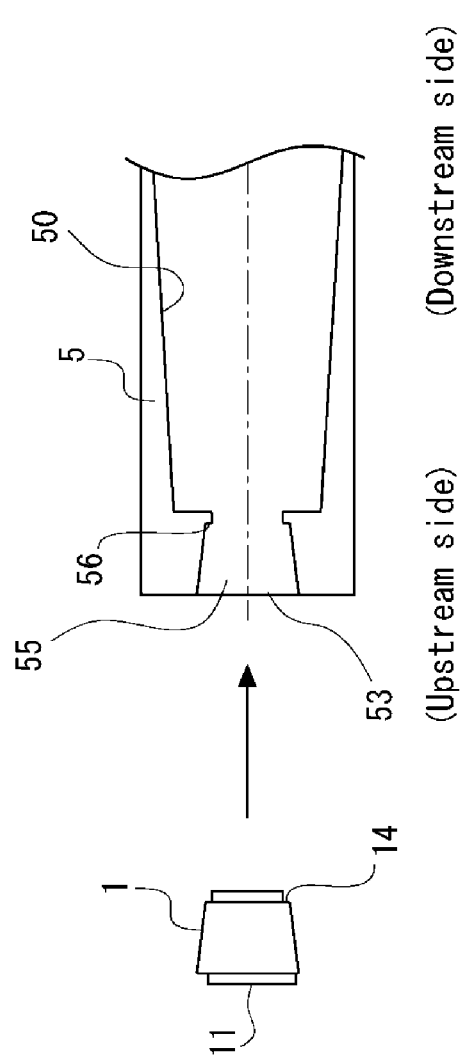

[Fig. 4]
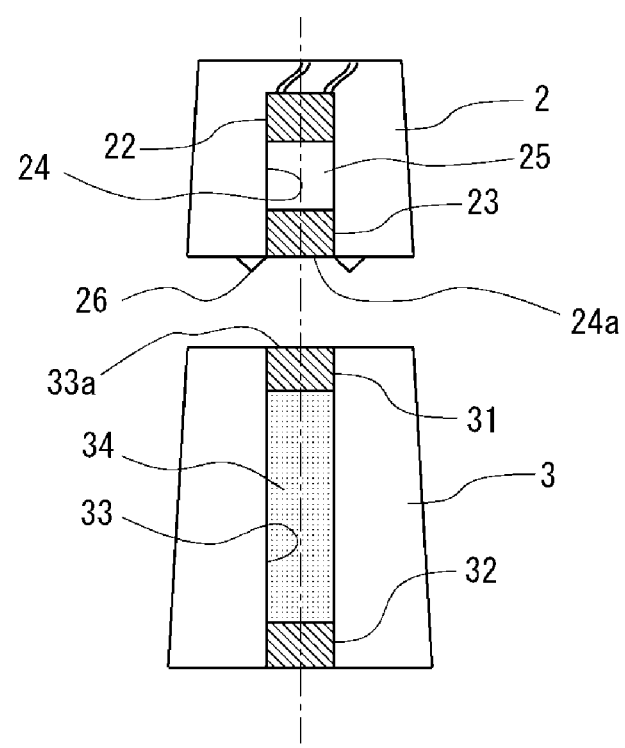

[Fig. 5]
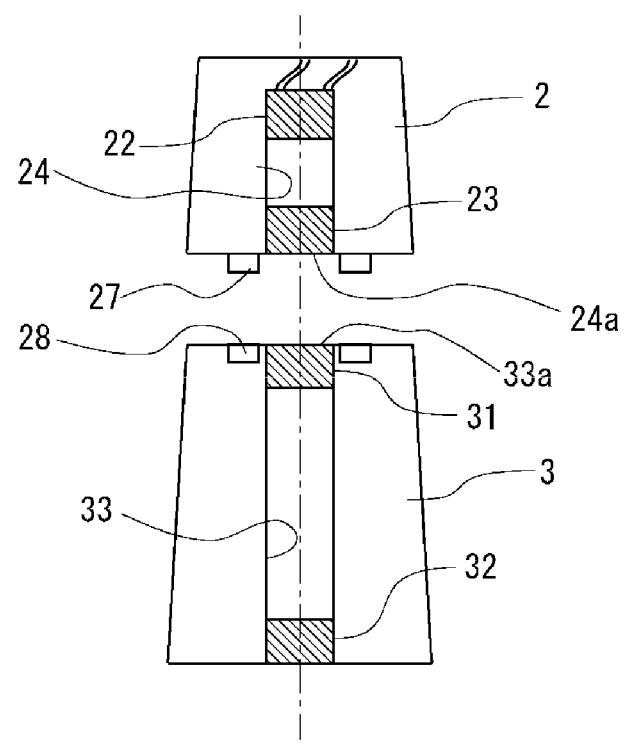

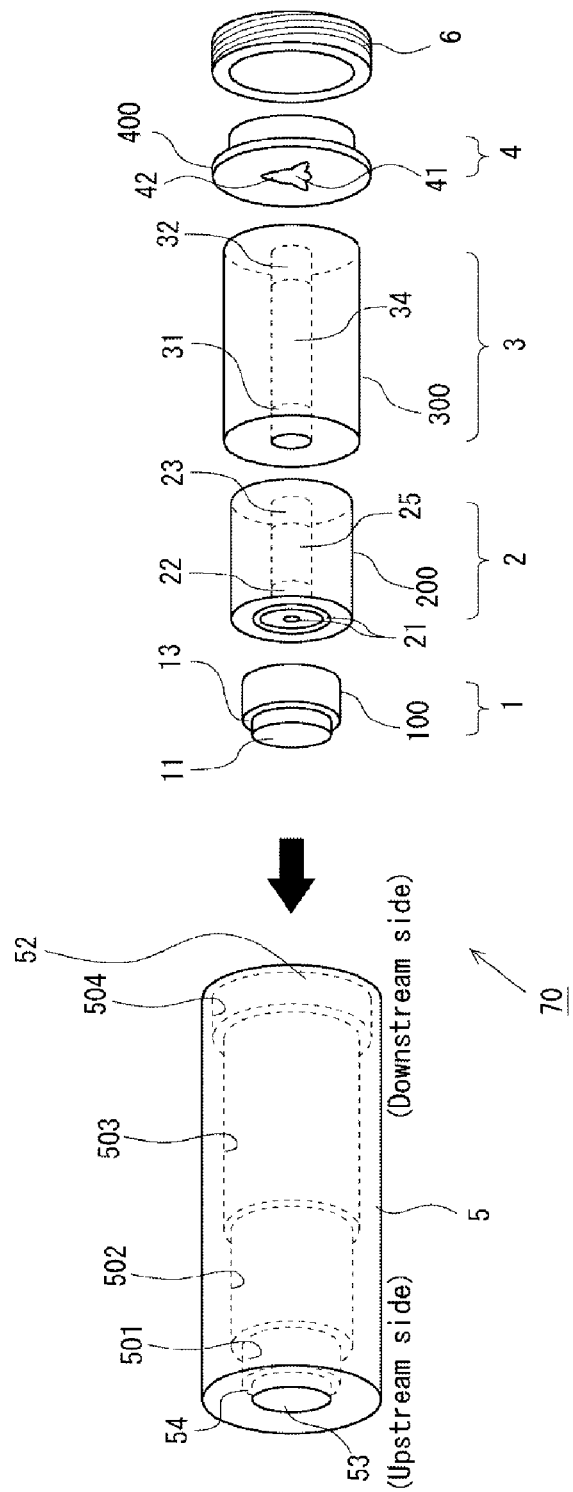
[Fig. 6]

SYRINGE

CROSS-REFERENCE TO RELATED APPLICATIONS

This application is a divisional of U.S. application Ser. No. 14/400,534, filed Nov. 11, 2014, which is the U.S. National Phase under 35 U.S.C. § 371 of International Application No. PCT/JP2013/063171 filed on May 10, 2013 which claims the benefit of Japanese Patent Application No. 2012-109863 filed on May 11, 2012, the entire contents of which are incorporated by reference herein.

The present invention relates to a syringe that injects an injection objective substance into an injection target area of a living body.

BACKGROUND ART

Needleless syringes perform injection without using an injection needle. They generally have a configuration in which pressure is applied to an injection liquid, which includes a medicine or the like, with the aid of a propellant, a pressurized gas, a spring, or the like. The pressure applied to the injection liquid is adjusted so as to deliver the injection liquid to a desired area inside a living body. Patent Document 1 discloses a configuration in which an injection liquid and a gas generating agent for applying pressure form one unit. The configuration also includes a lid that covers the unit. The unit is inserted into a syringe body before using the syringe. The inserted unit will be ready for injection when the lid is blocked. A new unit is loaded after the initial unit has been used. Thereafter, a subsequent injection procedure is performed.

Patent Document 2 discloses a configuration that includes an injection liquid holding portion and a pressurizing portion. The injection liquid holding portion retains an injection liquid. The pressurizing portion applies pressure to the injection liquid. The injection liquid holding portion is separated from the pressurizing portion. In this configuration, the injection liquid holding portion and a driving source of the pressurizing portion are replaced after the injection liquid is injected. Thereafter, a subsequent injection procedure is performed.

Patent Document 1: U.S. Pat. No. 6,258,063
Patent Document 2: Japanese Translation of PCT Application No. 2003-535654
Patent Document 3: US Patent Application Publication No. 2003/0114789

DISCLOSURE OF THE INVENTION

Regardless of presence of an injection needle, when an injection liquid is injected into an injection target area, injection conditions change depending on the subject person and the purpose of injection. The injection conditions include the kind and amount of injection liquid, the magnitude of load applied to the injection liquid in order to deliver the injection liquid to the injection target area. Thus, in order to perform injection under intended conditions, the syringe needs to have a configuration corresponding to the conditions. However, even the syringe having the above corresponding configuration may not be sufficiently convenient for a user to use it.

The present invention has been made in view of the problem. An object of the present invention is to provide a syringe that can facilitate liquid injection ideal for various purposes and improve a user's convenience.

In order to solve the problem, a syringe of the present invention includes a configuration that can regulate an order in which constituent portions of the syringe are loaded into a syringe housing. With this configuration, even if there is an error in the order of loading the constituent portions into the syringe housing, the user can immediately recognize the loading error. Thus, it is possible to improve the convenience of a user who uses a syringe.

Specifically, the present invention provides a syringe that injects an injection objective substance into an injection target area of a living body. The syringe includes a housing, a holding portion, a driving portion and a nozzle portion. The holding portion accommodates the injection objective substance. The driving portion applies injection energy toward the injection objective substance accommodated in the holding portion, from the holding portion. The nozzle portion includes a passage, through which the injection objective substance injected from the holding portion flows, and injects the injection objective substance from an open end of the passage to the injection target area. The holding portion, the driving portion, and the nozzle portion are loaded into the housing independently, such that the injection objective substance is ready for injection. The syringe further includes regulating means for regulating a loading position of the holding portion and the driving portion within the housing so that the holding and driving portions are always loaded in the same order into the housing for substance injection.

In the syringe according to the present invention, the holding portion, the driving portion and the nozzle portion are certain constituent portions of the syringe. The holding portion accommodates the injection objective substance. The driving portion applies an injection energy to the injection objective substance. The nozzle portion has a passage for injecting the injection objective substance. Substance injection is prepared when the three constituent portions are loaded into the housing in an independent manner. In the syringe, the driving portion applies injection energy to the injection objective substance accommodated in the holding portion. The injection objective substance flows through the passage of the nozzle portion and is injected to the injection target area from the open end of the passage. The injection objective substance contains a component which is expected to exhibit effects inside the injection target area. As described above, the injection energy applied by the driving portion is the driving source that performs the injection of the injection objective substance. Therefore, an accommodation state of the injection objective substance in the syringe and a specific physical form of the injection objective substance (a liquid or gel form, powder, granular solid) are not particularly limited, as long as the injection objective substance can be injected by the driving portion.

For example, the injection objective substance is a liquid and may be solid in a gel form, provided that the solid has such fluidity for injection. Further, the injection objective substance may be in a powder state. The injection objective substance may contain a component to be delivered to the injection target area of the living body. The component may exist in a state of being dissolved in the injection objective substance or may exist in a simply mixed state without being dissolved. Examples of the component to be delivered include vaccines for enhancing antibody, proteins for cosmetic treatments, and cultured cells for regenerating hair. These components are contained in fluid in a liquid or gel form so that the components can be injected, whereby the injection objective substance is formed.

Further, various energy sources can be used for allowing the driving portion to apply the injection energy to the injection objective substance as long as the injection objective substance can be injected. Examples of the injection energy source include an energy source which uses the pressure of gas generated with combustion of ignition charge and an energy source which uses an electric actuator (for example, a motor, a piezoelectric device, and the like) for applying pressure.

When the injection objective substance is supplied to a living body using the syringe according to the present invention, the kind of the injection objective substance used varies since the effects change depending on a size, an age, and a gender of the living body. Moreover, the thickness of the injection target area differs depending on the layer of biological tissues such as the epidermis layer, the intracutaneous layer, the subcutaneous layer, and the muscle layer. The load applied to the injection objective substance needs to be adjusted so that the injection objective substance reaches the respective depths. Thus, the holding portion, the driving portion, and the nozzle portion are configured to be independent from each other and are loaded into the housing in an independent manner.

A plurality of types of holding portions for accommodating a plurality of kinds and amounts of injection objective substances are prepared. Furthermore, a plurality of types of driving portions for applying a plurality of types of energy sources that supply the injection energy to the injection objective substance are prepared. These constituent portions are combined appropriately for the injection purposes and are assembled into the housing of the syringe. Further, a plurality of types of nozzle portions having various shapes may be prepared and included in the combination. This makes it easy to adjust a mode of injection of the injection objective substance. For example, the injection mode includes diameters of the passages for the injection objective substance injected into a plurality of positions of the injection target area. By combining the respective constituent portions of the syringe for appropriate injection purposes, the usability and convenience of the syringe according to the present invention are improved.

The plurality of types of driving portions may include different amounts, shapes, dimensions, and the like. Here, the energy source is an ignition charge or a gas generating agent and may be driving portions in which different amounts of gas are filled when the energy source is a pressurized gas. Further, the driving portions may have different spring constants when the energy source is a spring. Moreover, the plurality of types of holding portions may include different kinds, amounts, and the like in which injection objective substances are filled.

It may be possible to facilitate injection of the injection objective substance suitable for various injection purposes by appropriately combining the holding portion, the driving portion, and the nozzle portion and loading the same into the housing. However, the syringe may not function properly if there is an error in the order of loading the respective constituent portions in relation to the housing. In such a case, it may be desirable that users can recognize the error in the loading order immediately, which can enhance the convenience of the syringe. Moreover, by allowing users to load the respective constituent portions in a proper order, the syringe can allow for stable and reliable injection.

The syringe according to the present invention includes the regulating means that regulates the loading position of at least the holding portion and the driving portion in relation to the housing. When the holding portion and the driving portion are loaded into the housing, the relative loading position of the holding portion and the driving portion is determined at a predetermined position based on a configuration. In the configuration, the injection energy supplied from the driving portion is applied to the injection objective substance accommodated in the holding portion, so as to inject the injection objective substance. Thus, when the holding portion and the like are loaded at a position different from the predetermined position, the syringe cannot properly inject the injection objective substance. However, in the syringe according to the present invention, the loading position of the holding portion and the like to the housing is regulated uniquely by the regulating means. This can avoid a state where the holding portion and the driving portion are loaded in the housing at a position other than the regulated loading position. If there is an error in the order of loading the holding portion and the like, the user can recognize the loading error immediately. Thus, it is possible to realize various injection modes without degrading the user's convenience.

The holding portion may be disposed after used once and a new holding portion may be assembled to perform injection. Similarly, the driving portion and the nozzle portion may be disposed after used once and new driving and nozzle portions may be used. Alternatively, the driving portion and the nozzle portion may be used repeatedly if they allow for repeated uses. Since the housing of a syringe basically can be used repeatedly, it is not necessary to prepare a plurality of housings for various injection purposes and it is easy to maintain constituent components of the syringe is easy.

The holding portion and the driving portion to be regulated may be loaded into the housing while being temporarily fixed to each other by an adhesive tape or a paste, for example, before the two portions are loaded into the housing. Alternatively, the holding portion and the driving portion may be loaded into the housing individually. Moreover, the loading position of the nozzle portion may also be regulated by the regulating means. Since a nozzle portion includes a passage through which the injection objective substance is injected, the regulating means may also regulate the loading position of the nozzle portion.

The driving portion may include an ignition charge or a gas generating agent that combusts with a voltage, received from a power source portion, so as to generate a combustion gas. Furthermore, the driving portion may also apply the injection energy to the injection objective substance with pressure of the combustion gas. The regulating means may regulate a loading position of the power source portion, the holding portion, and the driving portion in relation to the housing so that the three constituent portions are always loaded in the same order into the housing. Since the relative loading position of the respective constituent portions is regulated by the regulating means, it is possible to efficiently realize various injection modes without impairing the user's convenience.

In the above aspect, although the loading position of the power source portion is regulated by the regulating means, the loading position of the power source portion may not be regulated by the regulating means. That is, when the power source portion is included in the syringe, the regulating means may regulate a loading position of the holding portion and the driving portion in relation to the housing as described above. Furthermore, a loading position of the power source portion may not be regulated by the regulating means when the power source portion is loaded into the housing. A voltage required for combustion of the ignition charge or the like may be applied to the driving portion multiple times depending on a storage capacity of the power source portion. In such a case, since it is not necessary to detach the power source portion from the housing whenever the injection objective substance is injected, the loading position of the power source portion may not be regulated by the regulating means. Moreover, depending on the storage capacity, the power source portion can be removed from the housing independently from the driving portion and the holding portion, thereby improving the convenience during replacement or the like.

The driving portion, the holding portion, and the nozzle portion may be formed so as to be superimposed in an axial direction of the housing when loaded into the housing. In this situation, the three constituent components are sequentially loaded from one direction into the housing through an opening of the housing. In this case, the regulating means includes a first tapered surface which is a continuous outer peripheral surface extending from the driving portion toward the holding portion when the three portions are superimposed on each other. A radius of the continuous outer peripheral surface increases as the outer peripheral surface advances from the driving portion toward the holding portion. The regulating means also includes a second tapered surface which is a continuous inner peripheral surface on the housing and corresponds to the first tapered surface.

The first and second tapered surfaces form the regulating means. The first tapered surface is formed when the driving portion, the holding portion, and the nozzle portion are superimposed on each other. The second tapered surface is provided on the housing to which the constituent portions are loaded. These tapered surfaces are formed so that the radii thereof increase as the tapered surfaces advance toward the opening of the housing through which the constituent portions are loaded. Since the radii increase in the order of the driving portion, the holding portion, and the nozzle portion, if a user tries to load the holding and nozzle portions into the housing prior to the driving portion, the nozzle portion will not advance in the housing beyond its own loading position. As a result, it is not possible to load the driving portion after the holding and nozzle portions are loaded. Thus, the user can recognize an error in the loading order of the constituent portions of the syringe.

Instead of using the tapered surfaces, the regulating means may include a first outer peripheral surface and a second inner peripheral surface. The first outer peripheral surface is a step-shaped outer peripheral surface and includes an outer peripheral surface of the driving portion and an outer peripheral surface of the holding portion, having a larger radius than a radius of the outer peripheral surface of the driving portion. The second inner peripheral surface is a step-shaped inner peripheral surface formed on the housing and corresponds to the first outer peripheral surface. The step-shaped outer peripheral surface and inner peripheral surface have different radii, since the outer peripheral surface is not continuous to the driving portion and the holding portion, and the inner peripheral surface of the housing corresponds thereto. Thus, it is possible to regulate the loading position of the driving portion and the holding portion. The driving portion and the holding portion may be disposed on the same axis in relation to the housing. Furthermore, the power source portion and the nozzle portion may be disposed on the same axis.

The syringe according to the present invention may employ another regulating means as long as it is configured such that, when a certain constituent portion is incorrectly loaded into the housing and reaches its original loading position, the loading of the other constituent portions is inhibited, whereby users can recognize an error in the loading order.

The driving portion may have a driving-side opening through which the injection energy is applied to the holding portion. The holding portion may have an accommodation hole in which the injection objective substance is accommodated. The accommodation hole may have an accommodation hole-side end portion that receives the injection energy received through the driving-side opening. In this case, an annular projection is formed on any one of the driving portion and the holding portion. The annular projection surrounds the driving-side opening or the accommodation hole-side end portion and deforms in the loading state to seal a space between the driving-side opening and the accommodation hole-side end portion. Alternatively, an annular groove is formed on any one of the driving portion and the holding portion. The annular groove surrounds the driving-side opening or the accommodation hole-side end portion and engages with the annular projection in the loading state to seal a space between the driving-side opening and the accommodation hole-side end portion.

The injection energy applied through the driving-side opening is transmitted to the accommodation hole-side end portion of the holding portion. The injection energy is subsequently applied to the injection objective substance accommodated in the accommodation hole. As described above, in the syringe according to the present invention, the driving portion and the holding portion are configured to be independent from each other and are loaded into the housing. With this configuration, if the injection energy is not appropriately applied between the driving portion and the holding portion, the injection objective substance is not properly injected to the injection target area. Thus, the deformable annular projection is provided on the driving portion or the holding portion. Furthermore, the annular projection and the annular groove, which are configured to engage with each other, are provided on the driving portion and the holding portion, respectively. Thus, it is possible to enhance the sealing of the space between the driving-side opening and the accommodation hole-side end portion and to suppress the injection transmitted from the driving portion from leaking outside. Moreover, it is possible to inject the injection objective substance to the injection target area satisfactorily.

EFFECT OF THE INVENTION

It is possible to provide a syringe that can facilitate injection of an injection liquid in various purposes, thereby enhancing the convenience of a syringe user.

BRIEF DESCRIPTION OF THE DRAWINGS

FIG. 1 is a cross-sectional view illustrating a schematic configuration in an assembled state, of a syringe according to a first embodiment of the present invention.

FIG. 2 is a diagram illustrating the order of loading constituent portions of the syringe illustrated in FIG. 1 and a relative relationship of the respective constituent portions.

FIG. 3 is a diagram for describing an embodiment in which the order of loading a power source portion of the syringe illustrated in FIG. 1 is different from the order of loading illustrated in FIG. 1.

FIG. 4 is a first diagram illustrating a detailed relative relationship between a driving portion and a holding portion of the syringe illustrated in FIG. 1.

FIG. 5 is a second diagram illustrating a detailed relative relationship between a driving portion and a holding portion of the syringe illustrated in FIG. 1.

FIG. 6 is a diagram illustrating the order of loading constituent portions of a syringe according to a second embodiment of the present invention and a relative relationship of the respective constituent portions.

BEST MODE FOR CARRYING OUT THE INVENTION

Hereinafter, a syringe 70 according to an embodiment of the present invention will be described with reference to the drawings. Although the syringe 70 is a so-called needleless syringe having no injection needle, the present invention can be applied regardless of presence of an injection needle. Moreover, the following embodiments are merely examples for description, and the present invention is not limited to the disclosed embodiments.

First Embodiment

FIG. 1 is a cross-sectional view illustrating a schematic configuration of the syringe 70 in a state where assembling of the syringe 70 is substantially completed. FIG. 2 is a diagram illustrating the order of loading the constituent portions thereof to assemble the syringe 70. As illustrated in FIG. 2, the syringe 70 has a housing 5 which serves as a main body thereof. The syringe 70 also includes a power source portion 1, a driving portion 2, a holding portion 3, and a nozzle portion 4, which are sequentially loaded into the housing 5. Finally, these constituent portions 1-4 are fixed to the housing 5 by a fixing ring 6. In this way, the syringe 70 is assembled.

Specifically, the housing 5 has a hollow shape. A loading opening 52 is formed at one end in an axial direction thereof so that the constituent portions 1-4 can be loaded in the housing 5. On the other hand, an opening 53 is formed at the other end in the axial direction of the housing 5. The opening 53 exposes, to the outside, an apex portion of a press button switch 11 (described later) provided in the power source portion 1 which is loaded first into the housing 5. Moreover, the housing 5 has a hollow portion having an inner peripheral surface which is formed as a continuous tapered surface 50. The tapered surface 50 is formed so that the radius (the inner diameter of the housing 5) thereof increases as the tapered surface advances from the opening 53 to the loading opening 52 (that is, along the axis of the housing 5). In the syringe 70 of the present embodiment, a side of the housing 5 close to the opening 53 is referred to as an upstream side and the side close to the loading opening 52 is referred to as a downstream side. This is based on the flowing direction when an injection liquid 34 is injected in a state where the respective constituent portions are loaded into the housing 5 and assembling of the syringe 70 is completed.

The constituent portions 1-4 have individual functions and formed independently. They are sequentially loaded into the housing 5 through the loading opening 52, and the loading state illustrated in FIG. 1 is formed. The power source portion 1 is a power supply for supplying power to an igniter 22 provided in the driving portion 2 described later. The power source portion 1 generates a voltage between power source-side electrodes 12 using the power of a battery included therein when a user presses the press button switch 11. The power source-side electrodes 12 are formed as a pair of electrodes including first and second projecting electrodes. The first projecting electrode is positioned on the central axis of the syringe 70 (the housing 5). The second projecting electrode is separated by a predetermined distance from the first electrode.

The driving portion 2 has a gas generating agent 25 therein. Pressure of a combustion gas is generated when the gas generating agent 25 combusts as injection energy for the injection liquid accommodated in the holding portion 3 described later. The driving portion 2 applies the generated pressure of combustion gas. Specifically, driving-side electrodes 21, corresponding to the power source-side electrodes 12 of the power source portion 1, are formed on an end surface of the driving portion 2. The driving-side electrodes 21 are formed as a pair of electrodes including first and second small circular electrodes. The first small circular electrode is positioned on the central axis of the syringe 70 (the housing 5). The second small circular electrode has the same radius as the predetermined distance, formed in a cylindrical form around the first small circular electrode. Since the driving-side electrodes 21 are formed in this manner, it is possible to maintain sufficient contact between the driving-side electrodes 21 and the power source-side electrodes 12. The sufficient contact can be maintained regardless of a relative position (the relative position in a rotation direction about the central axis of the syringe 70) of the power source portion 1 in relation to the driving portion 2.

The driving-side electrodes 21 are connected to the igniter 22 provided in the driving portion 2. The igniter 22 is a known electric ignition device. When the power source portion 1 applies a voltage between the driving-side electrodes 21, current flows and an ignition charge provided in the igniter 22 combusts. In this case, products generated by combustion of the ignition charge flow toward the gas generating agent 25 disposed in a combustion chamber 24 adjacent to the igniter 22. As a result, combustion of the gas generating agent 25 in the combustion chamber 24 starts. When a large amount of combustion gas is generated by combustion of the gas generating agent 25, pressure is applied to a metallic piston 23 provided adjacent to the combustion chamber 24. The piston 23 is propelled toward the downstream side of the syringe 70. In FIG. 1, an end portion of the combustion chamber 24 close to the holding portion 3, which is blocked by the piston 23, is a driving-side opening.

Examples of the ignition charge used in the igniter 22 preferably include a propellant (ZPP) containing zirconium and potassium perchlorate, a propellant (THPP) containing titanium hydride and potassium perchlorate, a propellant (TiPP) containing titanium and potassium perchlorate, a propellant (APP) containing aluminum and potassium perchlorate, a propellant (ABO) containing aluminum and bismuth oxide, a propellant (AMO) containing aluminum and molybdenum oxide, a propellant (ACO) containing aluminum and copper oxide, and a propellant (AFO) containing aluminum and iron oxide, or a propellant composed of a combination of a plurality of the propellants. These propellants exhibit such characteristics that, although the propellants generate hot and high-pressure plasma during combustion immediately after ignition, when combustion products condense at a room temperature, the propellants do not contain gaseous components and the pressure generated decreases abruptly.

Moreover, examples of the gas generating agent 25 disposed in the combustion chamber 24 preferably include a single base smokeless propellant including 98% by mass of nitrocellulose, 0.8% by mass of diphenylamine, and 1.2% by mass of potassium sulfate. Moreover, various gas generating agents used in a gas generator for airbags and a gas generator for seatbelt pretensioners may be used. A predetermined gas generated during combustion of the gas generating agent 25 contains gaseous components in a room temperature unlike the propellant. The gas generating agent 25 may not be used, and the igniter 22 and the piston 23 may form the driving portion 2.

The holding portion 3 accommodates the injection liquid 34 which is an injection objective substance injected by the syringe 70. Specifically, a through-hole (accommodation hole) 33 is formed at the center of the holding portion 3 so as to follow the central axis of the housing 5 in a state where the holding portion 3 is loaded into the housing 5 as illustrated in FIG. 1. Moreover, the injection liquid 34 is accommodated in the space of the through-hole 33 between an upstream plug 31 and a downstream plug 32. The upstream plug 31 and the downstream plug 32 are made from rubber, the surface of which is coated with a thin layer of silicon oil. As a result, the injection liquid does not leak when accommodating the injection liquid 34, and the injection liquid 34 can move inside the through-hole 33 smoothly with sliding of the piston 23 which will be described later. Moreover, an end portion of the through-hole (accommodation hole) 33 close to the driving portion 2, which is blocked by the upstream plug 31, is an accommodation hole-side end portion.

The nozzle portion 4 has a passage for injecting the injection liquid 34 accommodated in the holding portion 3 into an injection target (injection target area) outside the syringe 70. Specifically, a nozzle 43 for injecting the injection liquid 34 is formed in the nozzle portion 4. Furthermore, a recess 41 configured to accommodate the downstream plug 32 is formed in a portion of the nozzle portion 4 facing the downstream plug 32 in a state where the nozzle portion 4 is loaded into the housing 5 as illustrated in FIG. 1. The recess 41 has substantially the same diameter as the downstream plug 32 and has a slightly larger depth than the length of the downstream plug 32. With this structure, when pressure is applied to the injection liquid 34 due to injection energy from the driving portion 2, the downstream plug 32 can be accommodated in the recess 41. When the downstream plug 32 is accommodated in the recess 41, the pressurized injection liquid 34 is released from the space in the through-hole 33 of the holding portion 3. A passage 42 for guiding the released injection liquid 34 up to the nozzle 43 is formed so as to extend in a direction vertical to the central axis of the syringe 70. With this configuration, the released injection liquid 34 is injected from the nozzle 43 into the injection target through the passage 42. Moreover, since the recess 41 has such a depth that the downstream plug 32 is accommodated therein, it is possible to prevent the injection of the injection liquid 34 from being inhibited by the downstream plug 32.

A plurality of nozzles 43 or only one nozzle 43 may be formed in the nozzle portion 4. When a plurality of nozzles 43 are formed, passages 42 corresponding to the respective nozzles 43 are formed so that the released injection liquid is delivered to the respective nozzles 43. Further, the respective nozzles 43 are preferably disposed at equal intervals around the central axis of the syringe 70. Moreover, the diameter of the nozzle 43 is set appropriately by taking injection pressure applied to the injection liquid 34, properties (viscosity) of the injection liquid and the like into consideration.

As described above, in the syringe 70, the power source portion 1, the driving portion 2, the holding portion 3, and the nozzle portion 4 are formed independently from each other. Furthermore, the respective constituent portions 1-4 are sequentially loaded into the housing 5 as illustrated in FIG. 2, whereby the loading state illustrated in FIG. 1 is created.

In this manner, when the constituent portions of the syringe 70 are configured to be independent from each other, users can select constituent portions according to the purpose of injection and combine the constituent portions to assemble a final syringe 70. For example, a plurality of types of driving portions 2 having different kinds and amounts of gas generating agents 25 may be prepared. As a result, an injection depth of the injection target can be adjusted while changing a pressure profile applied to the injection liquid 34. Moreover, a plurality of types of holding portions 3 corresponding to different kinds and amounts of injection liquid may be prepared. As a result, the kinds and amount of the injection liquid 34 injected to an injection target can be adjusted according to the state or the like of the injection target. For example, the dose of injection liquid can be adjusted according to the injection target in such a way that the dose of injection liquid injected to the skin structure of adults is to be different from the dose of injection liquid injected to the skin structure of kids. Further, a plurality of types of nozzle portions 4 having different numbers of nozzles 43 and different nozzle diameters may be prepared so that an injection mode of the injection liquid 34 ideal for an injection target can be selected. A user selects one driving portion 2, one holding portion 3, and one nozzle portion 4 in order to attain an intended injection purpose. The user then loads the respective constituent portions into the housing 5 through the loading opening 52 as illustrated in FIG. 2 to create a state where the syringe 70 gets ready for use. In this way, it is possible to facilitate injection of injection liquid ideal for various purposes.

The respective constituent portions are preferably configured such that a predetermined unified paint or design is applied to the external shape thereof. As a result, users can easily select one driving portion 2, one holding portion 3, and one nozzle portion 4 to be loaded into the housing to be prepared for injection. For example, the driving portions 2 may be painted in blue, the holding portions 3 may be painted in yellow, and the nozzle portions 4 may be painted in red. In this way, users are prevented from selecting a plurality of driving portions 2 by mistake.

As illustrated in FIGS. 1 and 2, the power source portion 1 is loaded first into the housing 5. When the power source portion 1 is loaded into the housing 5 with the surface of the press button switch 11 facing the inside of the housing 5, a stepped portion 13 collides with a stepped portion 54. Here, the stepped portion 13 is provided around the press button switch 11 and the stepped portion 54 is provided around the opening 53 of the housing 5. With this configuration, a loading position of the power source portion 1 is determined. At this loading position, an apex surface of the press button switch 11 is flush with the end surface close to the opening 53, of the housing 5.

The syringe 70 is configured such that a voltage applied from the power source portion 1 is applied to the driving portion 2 to combust the gas generating agent 25 to generate a combustion gas. Furthermore, the injection liquid 34 is pressurized by the combustion gas, and the pressurized injection liquid 34 is injected outside from the nozzle 43. Thus, the constituent portions have to be loaded into the housing 5 in the order of the power source portion 1, the driving portion 2, the holding portion 3, and the nozzle portion 4 as illustrated in FIG. 2. If the constituent portions are not loaded in this order, it is not possible to inject the injection liquid 34 using the syringe 70.

Thus, the syringe 70 adopts a configuration for defining the loading position of the respective constituent portions in the housing 5 so that the respective constituent portions are loaded into the housing 5 in an appropriate order. That is, a user can recognize a loading error when the respective constituent portions are not loaded in an appropriate order. Specifically, the outer peripheral surfaces of the respective constituent portions are formed as a tapered surface (first tapered surface) so as to correspond to the tapered surface 50 (the second tapered surface) which is the inner peripheral surface of the housing 5. As described above, the tapered surface 50 is formed so that the radius (outer diameter) of the tapered surface 50 increases as the tapered surface advances from the upstream side to the downstream side. The outer peripheral surfaces 10, 20, 30, and 40 of the respective constituent portions are formed so as to correspond to the tapered surface 50 in the order of loading the same into the housing 5. That is, the outer peripheral surfaces of the four constituent portions 1-4 form a continuous tapered surface (first tapered surface) so as to correspond to the tapered surface 50 close to the housing 5 in a state where the respective constituent portions are superimposed in the housing 5 in the axial direction as illustrated in FIG. 1.

Since the outer peripheral surfaces 10, 20, 30, and 40 of the respective constituent portions are formed so as to form a continuous tapered surface when the outer peripheral surfaces are superimposed, the loading positions of the constituent portions in the housing 5 are uniquely determined as illustrated in FIG. 1 in order to create a state where the syringe 70 can be used. If the holding portion 3 is loaded into the housing 5 prior to the driving portion 2, the holding portion 3 cannot advance toward the deeper side (the upstream side) than a position where the outer peripheral surface 30 makes contact with a portion of the corresponding tapered surface 50. That is, a loading position is located where the holding portion 30 is to be loaded. With this structure, when the user tries to load the driving portion 2 subsequently, since a state where it is not possible to load the driving portion 2 is created, the user can immediately recognize where an error occurs in the loading order. Thus, the tapered surface 50 (second tapered surface) of the housing 5 and the continuous tapered surface (first tapered surface) correspond to the regulating means. Here, the continuous tapered surface is formed when the outer peripheral surfaces 10, 20, 30, and 40 of the constituent portions 1-4 are superimposed on each other.

When the respective constituent portions are loaded into the housing 5 as illustrated in FIG. 1, the fixing ring 6 is inserted into the housing 5 so as to make contact with the end surface of the nozzle portion 4 located closest to the downstream side. An external thread formed on the outer circumference of the fixing ring 6 engages with an internal thread 51 formed near the end portion (the loading opening 52) of the inner peripheral surface of the housing 5. In this way, the constituent portions loaded into the housing 5 can be pressed and fixed with the nozzle portion 4 interposed.

Modified Example 1

In the embodiment, the power source portion 1 is also loaded into the housing 5 through the loading opening 52 together with the other constituent portions. However, in place of such a configuration, the power source portion 1 may be loaded into the housing 5 from the upstream side separately from the driving portion 2 and the like. In this case, a stepped portion 14 is provided around an end surface of the power source portion 1 opposite the end surface where the press button switch 11 is provided. Moreover, a recess 55 in which the power source portion 1 is accommodated is formed in a portion of the housing 5 close to the opening 53. A projection 56 is provided in a space connecting the recess 55 and the space in the housing 5 defined by the tapered surface 50. When the power source portion 1 is loaded in the recess 55, the stepped portion 14 close to the power source portion 1 collides with the projection 56 close to the housing 5, whereby the loading position of the power source portion 1 is determined. The loaded power source portion 1 is fixed to the housing 5 by known fixing means. For example, the power source portion 1 can be detachable from the housing by a snap-fit of the power source portion 1. When the power source portion 1 is loaded into the housing 5 in this manner, the power source-side electrodes 12 are exposed to the space in the housing 5 defined by the tapered surface 50. Furthermore, the power source-side electrodes 12 can come into contact with the driving-side electrodes 21 of the driving portion 2 loaded through the loading opening 52 as illustrated in FIG. 1.

The power source portion 1 can supply an electric power to the driving portion 2 several times depending on the storage capacity. In this case, as illustrated in FIG. 1, it may be inconvenient to load the power source portion 1 into the housing 5 together with the other constituent portions such as the driving portion 2 whenever the injection liquid 34 is injected. Thus, it is possible to diminish inconveniences associated with loading of the power source portion 1 when the power source portion 1 is loaded separately from the other constituent portions as illustrated in FIG. 3. That is, the power source portion 1 does not have a tapered surface which is used for determining the loading position. After the power source portion 1 supplies electric power for a predetermined number of times corresponding to the storage capacity, the power source portion 1 may be detached from the housing and a new power source portion 1 may be loaded.

Modified Example 2

FIG. 4 illustrates a relative relationship between the driving portion 2 and the holding portion 3 according to the present modification. The gas generating agent 25 is disposed in the combustion chamber 24, and the gas generating agent 25 combusts with ignition of the igniter 22 to generate a combustion gas, whereby the piston 23 is pressed. In this case, the piston 23 moves from the opening (the driving-side opening) 24a close to the driving portion 3, of the combustion chamber 24 toward the holding portion 3. On the other hand, on the holding portion 3 side, the piston 23 advances into the end portion (the accommodation hole-side end portion) 33a of the through-hole 33 in which the upstream plug 31, the injection liquid 34, and the downstream plug 32 are disposed. This way, the injection energy due to the combustion gas of the gas generating agent 25 is transmitted to the injection liquid 34 with the upstream plug 31 interposed therebetween.

Here, an annular projection 26 is formed on the end surface of the driving portion 2, close to the holding portion 3, so as to surround the opening 24a. The annular projection 26 is formed from relatively soft metal such as aluminum. When the respective constituent portions are loaded into the housing 5 and are fixed by the fixing ring 6 to generate pressing force as illustrated in FIG. 1, the projection 26 collapses and deforms between the driving portion 2 and the holding portion 3 with the pressing force. With this deformation, the transmission of injection energy from the piston 23 to the upstream plug 31 is not inhibited. As a result, since the deformed annular projection 26 surrounds and seals the space between the driving portion 2 and the holding portion 3 around the through-hole 33 and the combustion chamber 24, it is possible to suppress the combustion gas of the gas generating agent 25 from leaking outside from the space between the driving portion 2 and the holding portion 3. It is also possible to allow the injection energy to be effectively transmitted to the injection liquid 34.

Modified Example 3

FIG. 5 illustrates a relative relationship between the driving portion 2 and the holding portion 3 according to the present modification. FIG. 5 illustrates a configuration in which an annular projection 27 and an annular groove 28 are formed instead of the annular projection 26 illustrated in FIG. 4. The FIG. 5 configuration allows injection energy to be effectively transmitted to the injection liquid 34. Specifically, the annular projection 27 is formed on an end surface of the driving portion 2, close to the holding portion 3, so as to surround the opening 24a. The annular projection 27 does not deform at the time of fixing to the housing 5 unlike the annular projection 26. Instead, the annular projection 27 engages with the annular groove 28 formed on an end surface of the holding portion 3, close to the driving portion 2, so as to surround the end portion 33a. The depth of the annular groove 28 is set to be slightly larger than the height of the annular projection 27.

As a result, when the annular projection 27 engages with the annular groove 28, the projection 27 and the groove 28 surround and seal the space between the driving portion 2 and the holding portion 3 around the through-hole 33 and the combustion chamber 24. Thus, it is possible to suppress the combustion gas of the gas generating agent 25 from leaking outside from the space between the driving portion 2 and the holding portion 3 and to allow the injection energy to be effectively transmitted to the injection liquid 34.

Second Embodiment

A second embodiment of the syringe 70 will be described based on FIG. 6. In this embodiment, the regulating means determines the loading position of the respective constituent portions loaded into the housing 5. Since the other constituent portions other than the regulating means, of the syringe 70 according to the second embodiment are the same as those of the syringe 70 according to the first embodiment, these constituent portions are denoted by the same reference numerals, and description thereof will be omitted.

In the present embodiment, the external shape of the power source portion 1, the driving portion 2, the holding portion 3, and the nozzle portion 4 loaded into the housing 5 are formed in an approximately cylindrical shape. Furthermore, the radii (outer diameters) of the outer peripheral surface of the respective constituent portions are designed so as to increase in the order of the outer peripheral surfaces 100-400 of the four constituent portions 1-4. Thus, in the present embodiment, when the respective constituent portions are superimposed so as to face each other in the housing 5, the outer peripheral surfaces of the respective constituent portions do not form a continuous tapered surface unlike the first embodiment but form a step-shaped discontinuous outer peripheral surface. The inner peripheral surface of the housing 5 is formed so as to correspond to the outer peripheral surfaces of the respective constituent portions. Specifically, four inner peripheral surfaces 501-504 are formed so as to respectively correspond to the outer peripheral surfaces 100-400 of the four constituent portions 1-4. The radii (inner diameters) of the inner peripheral surfaces 501-504 are set so as to increase in that order. Thus, the inner peripheral surface of the housing 5 is also formed as a step-shaped discontinuous surface.

Since the outer peripheral surfaces 100-400 form a step-shaped discontinuous outer peripheral surface when the constituent portions are superimposed and the inner peripheral surface of the housing 5 corresponds to the outer peripheral surface, the loading positions of the constituent portions are uniquely determined as illustrated in FIG. 1. With this configuration, users can recognize an error in the loading order immediately. Thus, the step-shaped discontinuous inner peripheral surfaces 501-504 and the step-shaped discontinuous outer peripheral surface correspond to a regulating means according to the present invention.

Moreover, the external shape of the respective constituent portions may have a circular truncated external shape so that the outer peripheral surface has a tapered surface instead of the cylindrical shape.

According to the syringe 70 of the present invention, for example, cultured cells, stem cells, and the like may be seeded or inoculated into injection target cells or scaffold tissues (scaffolds) in the field of the regenerative medicine of human, in addition to the case where the injection liquid is injected into the skin structure. For example, as described in Japanese Patent Application Publication No. 2008-206477, the syringe 70 may inject cells which may be appropriately determined by those skilled in the art depending on a transplantation portion and the purpose of the cell regeneration. For example, these cells include endothelial cells, endothelial precursor cells, myeloid cells, preosteoblast, chondrocytes, fibroblast, skin cells, muscle cells, liver cells, kidney cells, intestinal tract cells, and stem cells, as well as all cells considered in the field of the regenerative medicine. More specifically, a liquid (cell suspension) containing the cells to be seeded or inoculated is accommodated in the holding portion 3, and the liquid pressurized with combustion of the gas generating agent 25. In this way, predetermined cells are injected and transplanted to the transplantation portion.

Further, the syringe 70 according to the present invention may be also used for delivering DNA or the like to cells or scaffold tissues (scaffolds) as described in Japanese Patent Application Publication No. 2007-525192. In this case, it is possible to suppress an adverse effect on cells themselves or scaffold tissues (scaffolds) themselves when the syringe 70 according to the present invention is used, as compared with when the delivery is performed using a needle. Therefore, it can be said that the use of the syringe 70 according to the present invention is more desirable.

Further, the syringe 70 according to the present invention is ideally useful, for example, when various genes, cancer inhibiting cells, lipid envelops, and the like are directly delivered to target tissues and when antigen genes are administered to enhance the immunity against pathogens. In addition to the above, the syringe 70 can be also used, for example, in the field of medical treatment for various diseases (for example, see Japanese Translation of PCT Application No. 2008-508881 and Japanese Translation of PCT Application No. 2010-503616) and the field of immunological medical treatment (for example, see Japanese Translation of PCT Application No. 2005-523679). The field, in which the syringe 70 is usable, is not intentionally limited.

EXPLANATION OF REFERENCE NUMERALS

1: Power source portion
2: Driving portion
3: Holding portion
4: Nozzle portion
5: Housing
6: Fixing ring
10, 20, 30, 40: Outer peripheral surface
12: Power-side electrode
21: Driving-side electrode
22: Igniter
23: Piston
24: Combustion chamber
24a: Opening
25: Gas generating agent
26: Annular projection
31: Upstream plug
32: Downstream plug
33: Through-hole
33a: End portion
34: Injection liquid
41: Recess
43: Nozzle
70: Syringe
100, 200, 300, 400: Outer peripheral surface
501, 502, 503, 504: Inner peripheral surface

The invention claimed is:

1. A syringe that injects an injection objective substance into an injection target area of a living body, the syringe comprising:
a housing;
a holding portion that accommodates the injection objective substance;
a driving portion that applies injection energy toward the injection objective substance accommodated in the holding portion, from the holding portion, wherein the driving portion includes an ignition charge or a gas generating agent that combusts with a voltage applied from a power source portion and applies the injection energy to the injection objective substance with pressure of a combustion gas that is generated by combustion of the ignition charge or the gas generating agent;
a nozzle portion that includes a passage, through which the injection objective substance injected from the holding portion flows, and injects the injection objective substance from an open end of the passage to the injection target area, wherein the holding portion, the driving portion, and the nozzle portion are loaded into the housing independently, whereby a state where the injection objective substance can be injected is established; and
regulating means for regulating a loading position of the holding portion and the driving portion within the housing so that a loading state where the holding portion and the driving portion are always loaded in the same order into the housing is established for injection of the injection objective substance, wherein a loading position of the power source portion is not regulated by the regulating means when loading into the housing is implemented.

2. The syringe according to claim 1, wherein:
the driving portion, the holding portion, and the nozzle portion are formed so as to be superimposed in an axial direction of the housing when loaded into the housing, and the driving portion, the holding portion, and the nozzle portion are sequentially loaded from one direction into the housing through an opening of the housing, and
the regulating means comprises:
a first tapered surface which is a continuous outer peripheral surface formed so as to extend from the driving portion toward the holding portion when the driving portion, the holding portion, and the nozzle portion are superimposed on each other, and which is formed so that a radius of the continuous outer peripheral surface gradually increases from the driving portion toward the holding portion; and
a second tapered surface which is a continuous inner peripheral surface on a side of the housing and corresponds to the first tapered surface.

3. The syringe according to claim 1, wherein:
the driving portion, the holding portion, and the nozzle portion are formed so as to be superimposed in an axial direction of the housing when loaded into the housing, and the driving portion, the holding portion, and the nozzle portion are sequentially loaded from one direction into the housing through an opening of the housing, and
the regulating means comprises:
a first outer peripheral surface which is a step-shaped outer peripheral surface and includes an outer peripheral surface of the driving portion and an outer peripheral surface of the holding portion, which has a larger radius than a radius of the outer peripheral surface of the driving portion; and
a second inner peripheral surface which is a step-shaped inner peripheral surface formed on the housing and corresponds to the first outer peripheral surface.

4. The syringe according to claim 1, wherein:
the driving portion has a driving-side opening which is an opening for applying the injection energy to the holding portion,
the holding portion has an accommodation hole in which the injection objective substance is accommodated and the accommodation hole has an accommodation hole-side end portion that receives the injection energy applied from the driving-side opening, and
an annular projection, which surrounds the driving-side opening or the accommodation hole-side end portion and deforms in the loading state to seal a space between the driving-side opening and the accommodation hole-side end portion, is formed on one of the driving portion and the holding portion.

5. The syringe according to claim 1, wherein:
the driving portion has a driving-side opening which is an opening for applying the injection energy to the holding portion,
the holding portion has an accommodation hole in which the injection objective substance is accommodated and the accommodation hole has an accommodation hole-side end portion that receives the injection energy applied from the driving-side opening,
an annular projection which surrounds the driving-side opening or the accommodation hole-side end portion is formed on one of the driving portion and the holding portion, and an annular groove, which surrounds the driving-side opening or the accommodation hole-side end portion and engages with the annular projection in the loading state to seal a space between the driving-side opening and the accommodation hole-side end portion, is formed on the other one of the driving portion and the holding portion.

6. A syringe that injects an injection objective substance into an injection target area of a living body, the syringe comprising:

a housing;

a holding portion that accommodates the injection objective substance;

a driving portion that applies injection energy toward the injection objective substance accommodated in the holding portion, from the holding portion, wherein the driving portion includes an ignition charge or a gas generating agent that combusts with a voltage applied from a power source portion and applies the injection energy to the injection objective substance with pressure of a combustion gas that is generated by combustion of the ignition charge or the gas generating agent;

a nozzle portion that includes a passage, through which the injection objective substance injected from the holding portion flows, and injects the injection objective substance from an open end of the passage to the injection target area, wherein the holding portion, the driving portion, and the nozzle portion are loaded into the housing independently, whereby a state where the injection objective substance can be injected is established; and a regulator configured to regulate a loading position of the holding portion and the driving portion within the housing so that a loading state where the holding portion and the driving portion are always loaded in the same order into the housing is established for injection of the injection objective substance, wherein a loading position of the power source portion is not regulated by the regulating means when loading into the housing is implemented.

* * * * *